United States Patent [19]

Cordes et al.

[11] Patent Number: 4,668,232
[45] Date of Patent: May 26, 1987

[54] TRANSDERMAL DRUG PATCHES

[76] Inventors: Günter Cordes, Kurlandweg 13, D-5653 Leichlingen; Michael Wolff, Mozartstr. 28, D-4019 Monheim, both of Fed. Rep. of Germany

[21] Appl. No.: 810,212

[22] Filed: Dec. 18, 1985

[30] Foreign Application Priority Data

Dec. 22, 1984 [DE] Fed. Rep. of Germany ....... 3447072

[51] Int. Cl.$^4$ ............................................. A61K 9/00
[52] U.S. Cl. ................................................... 604/897
[58] Field of Search ............... 604/897, 896, 892, 890; 42/28, 349; 514/509, 964

[56] References Cited

U.S. PATENT DOCUMENTS

| | | | |
|---|---|---|---|
| 4,201,211 | 5/1980 | Chandrasekaran et al. | 604/897 |
| 4,346,709 | 8/1982 | Schmitt | 604/897 |
| 4,615,699 | 10/1986 | Gale et al. | 604/897 |

Primary Examiner—John D. Yasko
Attorney, Agent, or Firm—Dennis P. Clarke

[57] ABSTRACT

The invention relates to transdermal drug patches for the controlled release of drugs to the human skin, comprising
(a) an impermeable backing or covering layer,
(b) a reservoir layer adjacent to, and in close contact with said backing or covering layer, said reservoir layer comprising a polymer matrix composed of a rubber and an adhesive resin material wherein said therapeutically active agent or agents are wholly or partially soluble and which is permeable to said agent or agents,
(c) an adhesive layer adjacent to, and in close contact with, said reservoir layer and permeable to said therapeutically active agent or agents, and
(d) a protective layer covering and adhearing to said adhesive layer and removeable therefrom for the use of said transdermal drug patch, the improvement wherein said drug or drugs in the rubber and adhesive resin material of the reservoir layer are present together with a polymer capable of swelling in water and insoluble in the rubber and adhesive resin material of the reservoir layer, the quantity of said polymer being between 3 and 30% by weight of the rubber and adhesive resin mixture.

By the incorporation of this particular water-swellable polymer material in the rubber/adhesive resin mixture together with the drug which polymer material is insoluble in the matrix, in a particular proportion calculated to the weight of the rubber and adhesive resin material in particular the drug release from the patch to the skin is increased to twice or even more is achieved.

35 Claims, 3 Drawing Figures

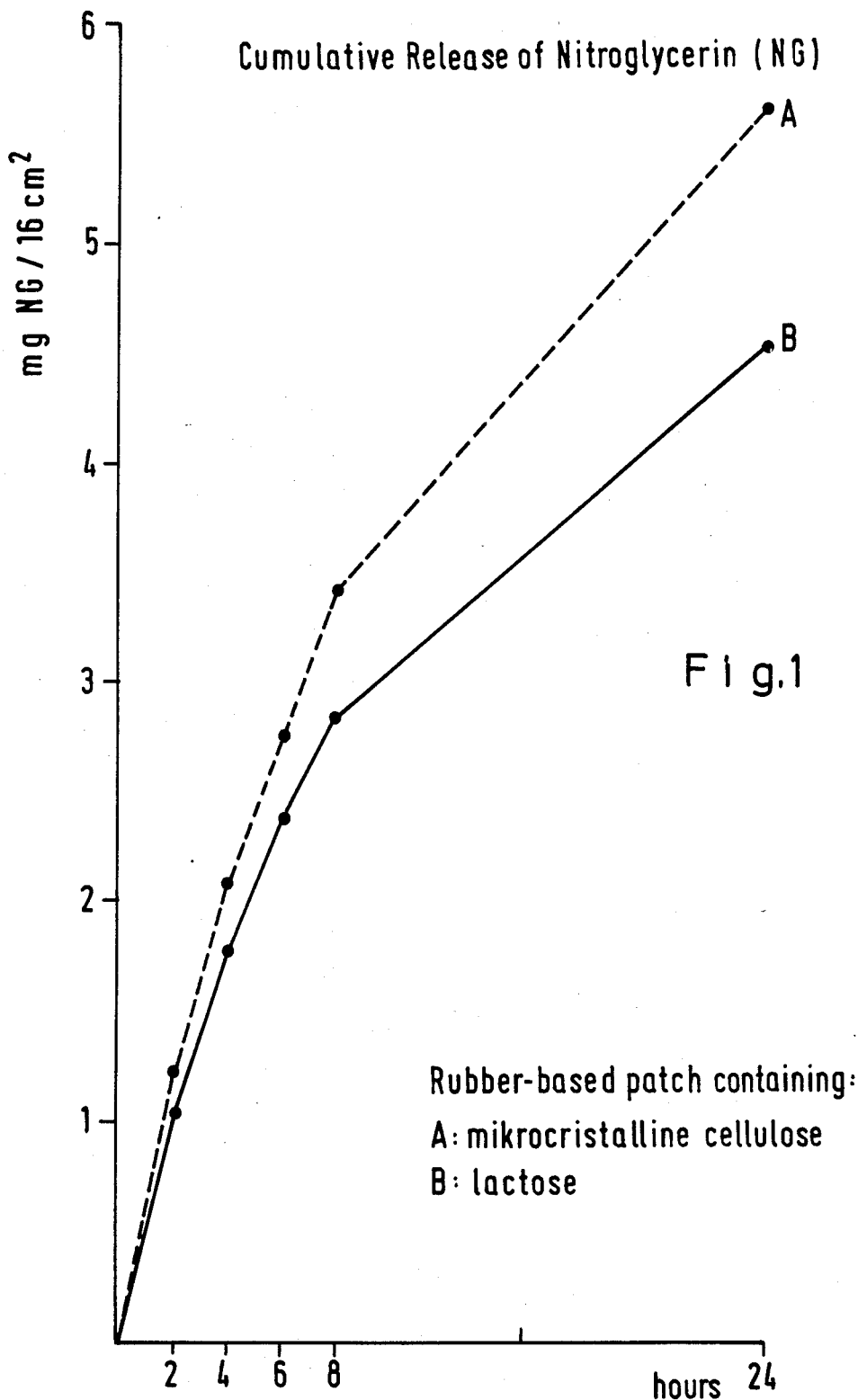

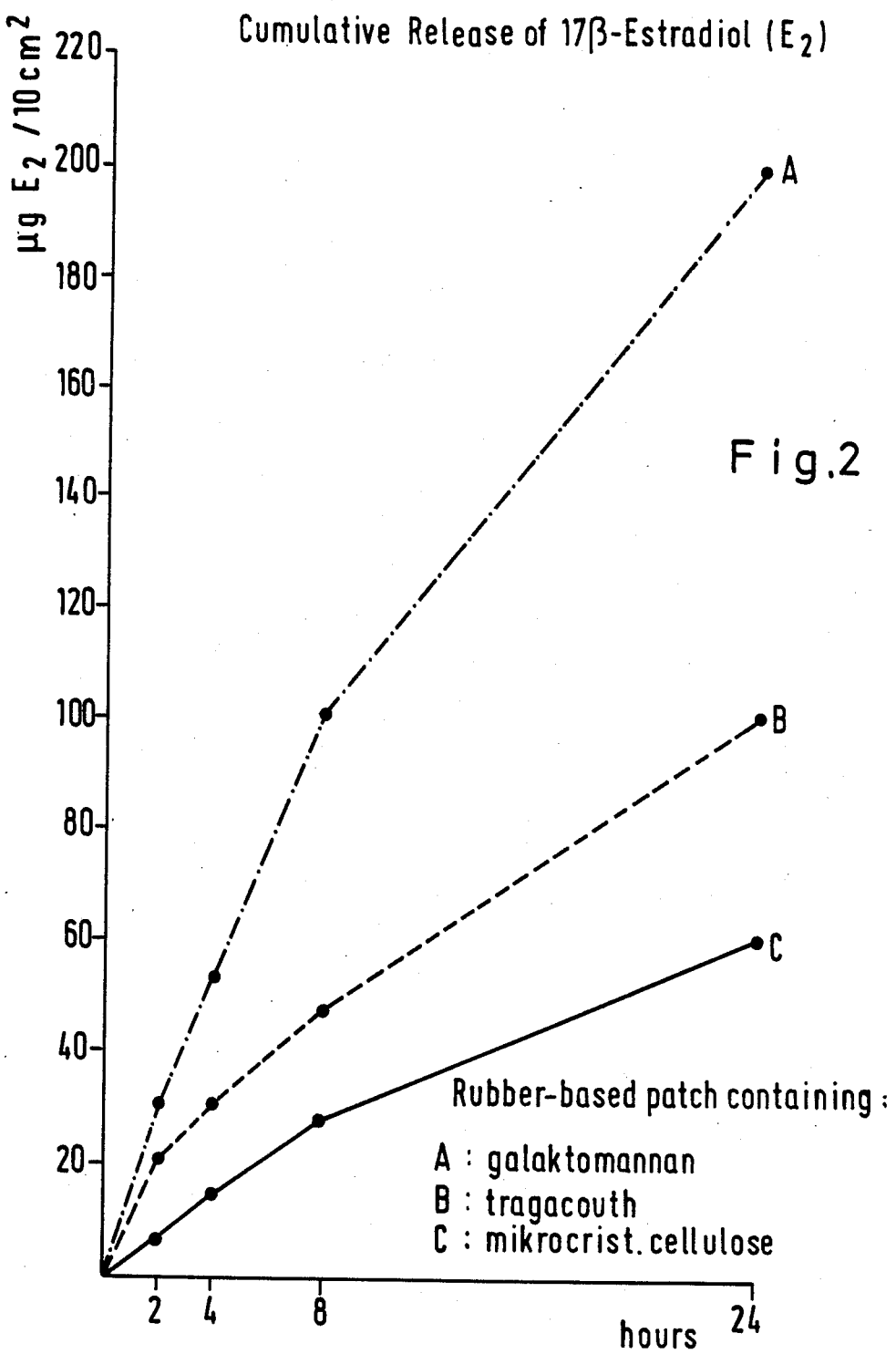

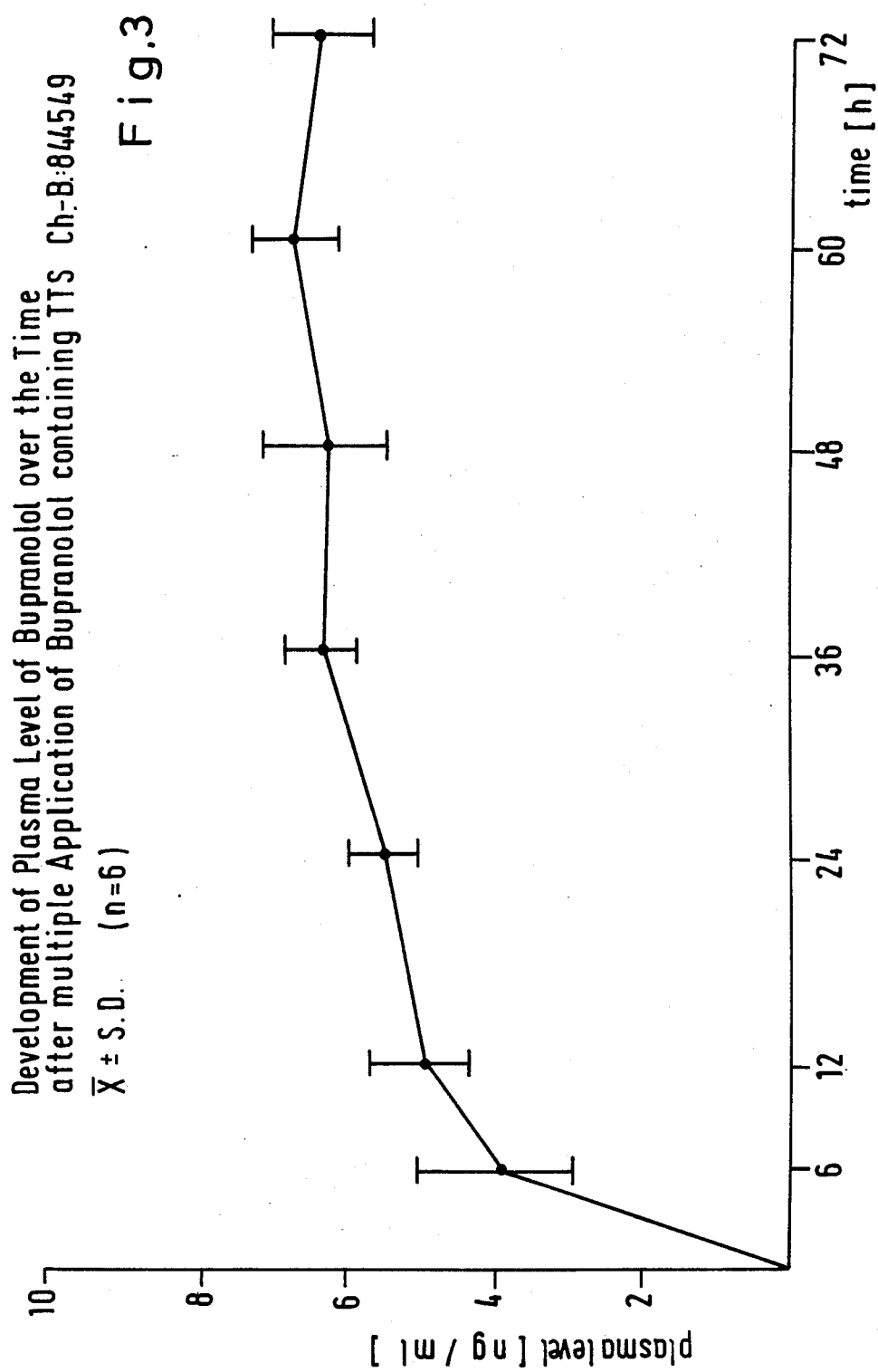

TRANSDERMAL DRUG PATCHES

The present invention relates to rubber-based patch formulations for the controlled administration to the skin over a relatively long period of drugs, including in particular beta blockers, steroid hormones, calcium antagonists and cardiac drugs, offering improved drug release properties and advantages in the development and manufacture of the patch film.

It is well known that formulations in which water-soluble drugs are dispersed in a water-insoluble matrix result in delayed release of the drug from the formulation. The cumulative quantity of drug released per unit time is usually proportional to the square root of the elapsed time, both for homogenous and for heterogenous matrices, whereby the release curve depends, among other things, on geometry of the presentation. Thus, as one moves from spherical systems towards film-shaped or (flat-)area systems, the release curve, i.e. the curve of drug released per unit time, becomes less and less steep, that is, the drug is released at an almost constant rate over a longer and longer period of time.

So-called transdermal drug-delivery patches, in which the drug is distributed within a thin, hydrophobic adhesive film, therefore represent a pharmaceutical formulation of simple design concept, capable of being manufactured in high volume, and in principle suitable for the transdermal method of administering drugs.

In practice however transdermal patches of this type as hitherto known are not usable for controlled transdermal delivery over relatively long periods. The thermodynamic activity of the drug in the base of the patch and in the patient's skin is not adequate, even with the hitherto known or proposed auxiliary control substances, to achieve the necessary rate of drug release and in particular also not adequate to achieve the desired long period of drug release action at an acceptable patch size.

If a larger quantity of the drug is incorporated into such a patch than the film-forming components of the patch can absorb, then the drug has to be distributed finely to amorphously in the adhesive matrix, so that the saturation condition of the adhesive can be maintained as well as possible by rapid redissolving of further quantities of the drug, thus minimising any fall-off in the rate at which the patch release the drug. In relation to the brush-coating methods in common use for manufacturing patch film, one possibility is to dissolve both the film-former and the drug in an organic solvent, to concentrate this solution down to a brushable viscosity, and then to brush this drug-containing adhesive solution out onto large-area strips and allow it to dry. However when volatile, liquid and/or crystalline drugs are used with the adhesive formulations commonly used for rubber patch film, this method gives rise to stability problems due to recrystallization and evaporation processes, which lead to uncontrolled and non-reproducible release of the drug and to impairment of the adhesive properties.

Furthermore, the galenical development of transdermal drug patches of this type is particularly difficult in practice because the patch formulation has to be optimised both for its adhesive properties and also for its permeability to the particular drug or drugs concerned.

An object of the present invention is thus to overcome the above-mentioned disadvantages of prior known transdermal drug patches both in respect of their drug-release properties and in respect of their manufacture and development, in particular in the sector of beta blockers, steroid hormones, calcium antagonists and cardiac drugs such as bupranolol, propranolol, estradiol, nitroglycerin and isosorbide dinitrate drugs, and to make available a transdermal drug patch assuring reproducible drug-release characteristics with a large total quantity of drug and, as far as possible, controlled release over the entire period of administration.

The transdermal drug patch according to the invention, for the controlled release of in particular in the above-mentioned drugs to the skin, consists as do the prior known transdermal drug patches of an impermeable covering layer to which is connected an adhesive film insoluble in water consisting of a mixture of rubber and adhesive resin based on natural or synthetic rubbers such as polyisobutylene, styrene-butadiene polymerisates, styrene isoprene polymerisates, styrene ethylene/bulylene polymerisates, or cis-1,4 polyisoprene together with a resin component such as colophonium and its derivates, polyterpene resins of β-pinene, hydrocarbon resins in which the drug or drugs are soluble and in which the drug or drugs are present partly in dissolved and partly in undissolved condition, and a protective layer which covers the adhesive film but which can be pulled off. The transdermal drug patch according to the invention is characterised by containing not only the drug or drugs but also one or more polymers capable of swelling in water (water-swellable polymers) in an amount of from 3 to 30 percent by weight of the mixture of rubber and adhesive resin containing the drug, these water-swellable polymers being insoluble in the mixture of rubber and adhesive resin.

Surprisingly, the inclusion in accordance with the invention of the water-swellable polymers, insoluble in the mixture of rubber and adhesive resin, increases the rate of drug release per unit time, and in particular the total quantity of drug released, by up to 100 percent or more. In contrast to this, it is known from the literature (cf. Y. W. Chien in J. R. Robinson "Sustained and Controlled Release Drug Delivery Systems", Chap. 4, pp. 255–256, published by Marcel Dekker, 1978) that the filter materials in common use in transdermal drug patch technology, such as silicon dioxide or zinc oxide in polymer matrix systems on a silicone basls or natural rubber, produce a lowering of the diffusion coefficient for solids and gases. Furthermore, in the manufacturing process the addition of the water-swellable polymers achieves stable binding of the excess quantity of drug in the adhesive material and/or an increase of viscosity of the adhesive solution used in manufacturing the transdermal drug patch in accordance with the invention, and also achieves an improvement of the coherence and adhesive properties of the adhesive film.

Examples of the water-swellable polymers which in accordance with the invention are added to the mixture of rubber and adhesive resin are products such as galactomannans, cellulose products, tragacanth, polyglycosides, polyvinylpyrrolidones, finely powdered polyamides, water-soluble polyacrylamide, carboxyvinyl polymerisates, agar-like algae products, mixed polymerisates of methyl vinyl ether and maleic acid anhydride, guar rubber, types such as hydroxyphenyl-guar rubber or guar powder, gum arabic, dextrin and dextran, microbiologically produced polysaccharide rubber such as polysaccharide B-1459 or the highly water-soluble type Keltrol or synthetically produced polysaccharides such as the product Ficoll, methyl glucose derivatives, hydroxymethylpropyl cellulose, polycalacturonic acide derivatives such as pectin or the amidated product Pectinamid. Galactomannans, microcrystalline cellulose and tragacanth are especially suitable and, therefore, are preferred. Galactomannans and tragacanth are very especially suitable and most preferred for the steroid hormone estradiol and microcrystalline cellulose is very specially suitable and most preferred for bupranolol and for nitroglycerin.

According to a particular and preferred embodiment of the present invention, the matrix composed of rubber and adhesive resin is subdivided into a matrix layer which does contain the active agent and the water-swellable polymer, an adhesive layer which does or does not contain active agent and a separating layer between the two above layers, which is completely permeable to the rubber/adhesive resin mixture as well as to the active agent contained therein but completely impermeable or only partly permeable to the water-swellable polymer. The embodiment with this separating layer is preferred in case the adhesive resin film is subdivided into a said matrix layer and said adhesive layer.

As the following examples 1 to 10 show, the water-swellable polymers used in adhesive film based on a mixture of rubber and adhesive resin in accordance with the invention have a decisive effect on the drug release properties for lipophilic drugs. The therapeutically desirable release curve can for a particular drug be advantageously achieved by choosing one of the products specified in the invention from among the group of water-swellable polymers, by (choosing) the concentration of these products, and by using various different combinations of these products within the limits specified for the invention, without having to change to a different base material for the patch. Particularly in the case of nitroglycerin and isosorbide dinitrate, the literature states that when using simple adhesive tapes containing the drug in dissolved form there is a risk of too rapid, uncontrolled drug release and a risk of problems in stability, dosage and handling (cf. DE-OS (German published application No. 3 200 369). The therapeutically necessary quantity can then only be achieved by using a large-area patch or the adhesive base does not adequately bind the drug, so that the drug is released too quickly for long-acting therapy.

Conventional manufacturing methods, in which the patch components are dissolved or dispersed in an organic solvent until the brushing-out viscosity necessary for production purposes is achieved, can lead to the formation of an unslable, oversaturated system because a larger quantity of the drug is initially dissolved than the sorption capacity of the film-forming components. In this case, particularly with volatile substances, substantial losses of content occur even already during the drying process, and/or the excess amount of drug crystallizes out in the adhesive film during storage. In the transdermal drug patch according to the invention, these problems are circumvented by using insoluble products which have the property of being able to bind the drug during evaporation and conventration. This also achieves a fine distribution of the drug within the adhesive matrix, and makes it possible to incorporate a larger guantity of the drug than that permitted by the saturation solubility of the film-forming components. By brushing-out the adhesive solution onto a web which is unpermeable or only partly permeable to the water-swellable polymer or said polymer having adsorbed thereto the active agent an increase in concentration or, respectively, a higher concentration of active agent and/or the water-swellable polymer is produced in this rubber adhesive resin layer in a simple manner if it is desired because of reasons of adhesive properties of the adhesive layer and/or because of biopharmaceutical reasons.

The use of a web material permeable to the adhesive resin material renders unnecessary the application of an additional adhesive layer. In order to produce sufficient adhesive properties in the adhesive layer of the transdermal drug patch according to the invention or to allow the application of the impermeable cover layer, such an additional adhesive layer would have been necessary depending upon the concentration in the water-swellable polymer.

The transdermal drug patch in accordance with the invention is manufactured as follows: The components of the mixture of rubber and adhesive resin are dissolved in an organic solvent; into this solution the drug, together with a water-swellable polymer not soluble in the mixture of rubber and adhesive resin or its solution, i.e. not soluble in the adhesive film, in a proportion of between 3 and 30 percent by weight of the mixture of rubber and adhesive resin, is dispersed, the dispersion, after if necessary evaporating off some of the solvent to achieve a brushable consistency, is coated onto an abhesive protective film made of material commonly used for the manufacture of pull-off protective layers for transdermal drug patches, moot of the solvent is evaporated off, a covering layer of materials in common use for transdermal drug patches is applied, and the resulting patch film is then cut into patches of a size necessary and/or suitable for the intended use. This is done in such a way that the components of the mixture of rubber and adhesive resin together with the drug and the water-swellable polymers not soluble in adhesive film and the organic solvent are mixed intimately before further processing of the drug-containing polymer matrix thus produced.

If necessary the process of coating the patch material containing the dispersion agent is performed in several stages in order to attain the specified coat weight per unit area. In such cases, most of the dispersing agent is cleaned off before the next coat is applied.

The possibilities of controlling the drug release from a rubber patch by means of the water-swellable polymers of the type proposed by the invention are surprising. As Examples 1 and 2 demonstrate, it is possible by this means, for example, to increase the rate of drug release without altering the concentration of the drug in the patch.

EXAMPLE 1

Nitroglycerin patches in accordance with the present invention with microcrystalline cellulose in a dispersion zone formed of layers are manufactured as follows:

An adhesive material free of nitroglycerin and microcrystalline cellulose consisting of
- 1.018 g of polyisobutylene (mean molecular weight 900,000 to 1,400,000; trade product OPPANOL B 100),
- 0.916 g of a solid aliphatic hydrocarbon resin (trade product PICCOTAC CBHT),
- 0.916 g of hydrogenated rosin resin (trade product ABITOL), 0.094 g of a triglycerid of medium-size chain in the ether hydrocarbon group (trade product MIGLYOL 812), 32 g of n-hexane as solvent.

This product is coated onto a protective layer having an aluminum layer unilaterally vapour deposited thereupon and coated on both sides with an abhesive layer such that after evaporation of the solvent an adhesive layer of about 4.5 mg/cm² is obtained. Onto the so obtained adhesive layer there is produced a dispersion (matrix) layer containing nitroglycerine and microcrystalline cellulose said layer having a weight per square unit of about 19.2 mg/cm².

This layer is produced as the above adhesive layer consisting of 2.2671 g of polyisobutylene (mean molecular weight 900,000 to 1,400,00; trade product OPPANOL B 100), 2.0409 g of solid aliphatic hydrocarbon resin (trade product PICCOTAC CBHT), 2.0409 g of hydrogenated rosin resin (trade product ABITOL), 0.2071 g of a triglyceride of medium-size chain in the ether hydrocarbon group (trade product MYGLYOL 812), 5.700 g of a 5 percent (w/w) solution of nitroglycerine-microcrystalline cellulose-distribution (trade product 5 percent distribution product nitroglycerine/AVICEL pH 105)

38 g of n-hexane.

After covering the dispersion layer with an impermeable covering layer, the resulting patch film is divided into individual patches suitable for therapeutic use.

EXAMPLE 2 (COMPARISON EXAMPLE)

Manufacture is performed as in example 1 except that the trituration of nitroglycerin and cellulose is replaced by a 5 percent trituration of nitroglycerine and lactose.

DRUG RELEASE

Pieces of patch film of size 16 cm² manufactured in accordance with Examples 1 and Z are immersed in isotonic sodium chloride solution at 37° C. and the guantity of nitroglycerine released after 2, 4, 6, 8 and 24 hours respectively is measured by liquid chromatography. The volume of the release medium is chosen to assure that sink conditions are maintained throughout the test.

The results are shown in FIG. 1.

EXAMPLE 3

A patch containing the drug estradiol using galactomannan (trade product MEYPROGAT 90) as water-swellable polymer in an adhesive dispersion layer is manufactured as follows:

The adhesive material containing estradiol and having the constituents and proportions of solvents listed in Table 1 (formulations A, B, C, D) is coated onto a protective layer of which one side is vapour-deposited with aluminum and both sides are abhesive in such a way that after evaporating off the solvent an adhesive film with the weights per unit area specified in Table 1 is attained.

After applying a covering layer to cover this adhesive layer containing estradiol and galactomannan, the patch film is divided into individual pieces suitable for therapeutic use.

TABLE I

Composition of estradiol patches containing galactomannan

| Constituent | Quantity (g per 1000 cm²) Formulation | | | |
|---|---|---|---|---|
| | A | B | C | D |
| 17 β-estradiol micron. (particle size < 9 μm) | 0.42 | 0.3 | 0.27 | 0.5 |
| galactomannan (product MEYPROGAT 90) | 1.5 | 0.9 | 0.9 | 0.5 |
| polyisobutylene (product OPPANOL B 100) | 3.0 | — | — | — |
| hydrated colophonium (rosin resin) (product ABITOL) | 3.0 | — | 1.5 | — |
| solid hydrogenated hydrocarbon resin (product PICCOTAC CBHT) | 3.0 | — | — | — |
| three-block polystyrene/polyisoprene/polystyrene copolymer (product CARIFLEX TR 1107) | — | 1.7 | 1.7 | 1.7 |
| solid aromatic hydrocarbon resin (product PICCOVAR L 60) | — | 2.2 | 2.2 | 2.2 |
| polyterpene resin (product DERCOLYTE S 10) | — | 1.5 | — | 1.5 |
| 1.2-propandiol | 0.5 | 0.15 | 0.15 | 0.2 |
| triglyceride (product MIGLYOL 812) | 0.5 | — | — | — |
| special benzine 80–100 | 64 | 19 | 19 | 19 |
| weight per unit area, mg/cm² | 11.9 | 6.75 | 6.72 | 6.60 |

For comparison purposes a series of estradiol patches to compositions corresponding to formulations A, B and C above but excluding the ingredient galactomannan were also manufactured. Table 2 gives the constituents and solvent used and the weights per unit area of these adhesive films containing no polymers. The deviations over the products given in Table 1 are partly due to procedural necessities, partly due to biopharmocological reasons. The patches were produced with the aim to get a release of a active agent as high as possible.

TABLE 2

Composition of estradiol patches not containing galactomannan

| Constituent | Quantity (g per 1000 cm²) Formulation | | |
|---|---|---|---|
| | A' | B' | C' |
| 17 β-estradiol micron. (particie size < 9 μm) | 0.39 | 0.51 | 0.51 |
| polyisobutylene (produot OPPANOL B 100) | 1.95 | — | — |
| hydrated colophony (product ABITOL) | 2.34 | — | 1.19 |
| solid hydrated hydrocarbon resin (product PICCOTAL CBHT) | 2.34 | — | — |
| three-block polystyrene/polyisoprene/polystyrene copolymer (product CARIFLEX TR 1107) | — | 1.32 | 1.32 |
| solid aromatic hydrocarbon resin (product PICCOVAR L 60) | — | 1.98 | 1.98 |
| polyterpene resin (product DERCOLYTE S 10) | — | 1.19 | — |
| 1.2-propandiol | 0.39 | 0.10 | 0.10 |
| triglyceride (product MIGLYOL 812) | 0.39 | — | — |
| weight per unit area, mg/cm² | 7.8 | 5.1 | 5.1 |

DRUG RELEASE IN VITRO

The measurement was made by the method of examples 1 and 2 using patches of 10 cm² size and a temperature of 34° C. The cumulative drug release rates from patches A, B and C manufactured in accordance with the invention are compared in Table 3 with the cumulative drug release rates from comparison patches A', B' and C' which contained no galactomannan but were otherwise identical.

It is evident that the inclusion of galactomannan as water-swellable polymer in an estradiol patch film of single-layer structure has the effect of increasing the cumulative release rate of estradiol ($=E_2$).

TABLE 3

| | Release of $E_2$ (μg per 10 cm²), n = 2 | | | | | |
|---|---|---|---|---|---|---|
| | Formulations | | | | | |
| Time (h) | A | A' | B | B' | C | C' |
| 2 | 47.4 | 17.5 | 42.7 | 35.3 | 70.1 | 36.6 |
| 4 | 79.1 | 33.7 | — | — | — | — |
| 6 | 108.2 | — | — | — | — | — |
| 8 | — | 55.4 | — | — | — | — |
| 24 | 252.1 | 123.4 | 323.3 | 182.5 | 395.4 | 229.9 |

DRUG RELEASE IN VIVO (a) 1 patch of 10 cm² produced according to the above Formulation B,
(b) 2 patches of 10 cm² produced according to the above Formulation D, have been applied to the lateral chest of two test persons. After 72 hours the patches were removed and the estradiol content which remained in the patch was determined chromatographically. The in-vivo drug release rate so determined with regard to a singular patch of 10 cm² is:

(a) 203 μg with test person 1 and Formulation B
(b) 208 μg with test person 1 and Formulation D
(c) 92.5 μg wlth test person 2 and Formulation B
(d) 110 μg with test person 2 and Formulation D.

BIOAVAILABILITY

In the above in-vivo test blood samples have been collected 48, 38, 24, and 14 hours as well as immediately before the patches have been applied to the skin of the test persons. Concentration of estradiol in blood plasma of the test person was determined by radioimmunology. After the application of the patches, blood samples were collected after 10, 24, 34, 48, 58, and 72 hours and estradiol concentration in blood plasma again was determined by radioimmunology. On an average, the following increase in estradiol concentration in the blood plasma of the tested persons was determined (referring to one patch of 10 cm²):

(a) 6.45 pg/ml with test person 1 and Formulalion B
(b) 6.65 pg/ml with test person 1 and Formulation D
(c) 3.90 pg/ml with test person 2 and Formulation B
(d) 1.47 pg/ml with test person 2 and Formulation D.

These results show that
the application of an estradiol patch produces an increase of estradiol concentration in the blood plasma in men,
decreasing the estradiol content but increasing the galactomannane content (Formulation B over Formulation D of Example 3) produced in-vivo an increased mean estradiol concentratlon in blood.

EXAMPLE 4

A patch for administering the drug bupranolol in accordance with the present invention with microcrystalline cellulose (product AVICEL pH 105) as the water-swellable polymer in an adhesive dispersion layer is manufactured as follows:

The rubber/adhesive material containing bupranolol and consisting of the components given in Table 4 (Formulation A) is coated into subsequent steps onto a protective layer of which one side is vapour-deposited with aluminum and both sides are abhesive in such a way that after evaporating off the solvent and adhesive film of 14.7 mg/cm² is obtained.

After applying an impermeable covering layer to cover the above-mentioned adhesive layer containing bupranolol and microcrystalline cellulose, the patch film is divided into individual pieces suitable for therapeutic use.

EXAMPLE 5 (COMPARATIVE EXAMPLE):

The production follows example 4 without however using microcrystalline cellulose as water-swellable polymer. The weight per unit area in the resulting film is 13.5 mg/cm². The composition and amounts of solvents used in the adhesive matrix layer are given in Table 4.

TABLE 4

Composition of bupranolol patches containing microcrystalline cellulose as water-swellable polymer or not (Examples 4 and 5)

| | Quantity (g per 1000 cm²) Formulation | |
|---|---|---|
| Constituent | A containing polymer | B without polymer |
| bupranolol micron. (particle size < 50 μm) | 1.2 | 1.2 |
| microcrystalline cellulose | 1.2 | — |
| polyisobutylen (product OPPANOL B 100) | 3.71 | 3.71 |
| solid aromatic hydrocarbon resin (product PICCOVAR L 60) | 6.69 | 6.69 |
| 1.2-propandiol | 0.5 | 0.5 |
| solid paraffine | 1.4 | 1.4 |
| special benzine 80–110 | 55 | 55 |

DRUG RELEASE:

The determination is effected as described in Example 1 for the nitroglycerine containing patches. The cumulative release rates of the bupranolol patch according to the invention and Example 4 and that of the patch free of microcristalline cellulose according to Example 5 are compared in Table 5.

As is shown, the addition of microcristallines cellulose as water-swellable polymer to the single layer bupranolol patch film produces an increase of the cumulative rates of release of active agent.

TABLE 5

| Bupranolol-release (mg/25 cm²), n = 2 | | |
|---|---|---|
| Time (h) | Example 4 | Example 5 |
| 2 | 6.46 | 4.04 |
| 4 | 10.04 | 5.77 |
| 8 | 15.37 | 8.21 |
| 24 | 26.95 | 14.20 |

EXAMPLE 6

A rubber-based estradiol patch with polymers which swell to differing extents in water is manufactured as follows.

The adhesive material containing estradiol, comprising the constituents and solvent proportions given in Table 6 (Formulations A, B and C) is coated onto a protective layer of which one side is vapour-deposited with aluminum and both sides are adhesive in such a way that after evaporating off the solvent an adhesive film of the respective weights per unit area quoted in Table 6 is attained.

After applying an impermeable covering layer to cover the above-mentioned adhesive layer containing estradiol and swellable material, the patch film is divided into individual pieces suitable for therapeutic use.

TABLE 6

Composition of estradiol patches containing various different water-swellable polymers

| Constituent | Quantity (g per 3000 $cm^2$) Formulation | | |
|---|---|---|---|
| | A | B | C |
| 17 β-estradiol micron (particle size < 9 μm) | 1.5 | 1.5 | 1.5 |
| galactomannane (product MEYPROGAT 90) | 1.5 | — | — |
| tragacanth | — | 1.5 | — |
| microcrystalline cellulose (product AVICEL pH 105) | — | — | 1.5 |
| three-block polystyrene/ polyisoprene/polystyrene copolymer (product CARIFLEX TR 1107) | 5.1 | 5.1 | 5.1 |
| solid hydrated hydrocarbon resin (product PICCOTAC CBHT) | 6.6 | 6.6 | 6.6 |
| polyterpene resin (product DERCOLYTE S 10) | 4.5 | 4.5 | 4.5 |
| 1.2-propandiol | 0.6 | 0.6 | 0.6 |
| special benzine 80–100 | 27 | 27 | 27 |
| weight per unit area, mg/$cm^2$ | 6.6 | 6.6 | 6.6 |

Table 7 shows the time variation of the water absorption of the polymer products in a saturated water vapour atmosphere at room temperature as a percentage of the weight of the specimen.

TABLE 7

| Test substance | Water absorbed in | | |
|---|---|---|---|
| | 48 h | 96 h | 168 h |
| galactomannan (product MEYPROGAT 90) | 69.72 | 97.86 | 113.14 |
| tragacanth | 68.08 | 84.51 | 96.7 |
| microcrystalline cellulose | 14.7 | 16.7 | 21.5 |

DRUG RELEASE:

FIG. 2 shows the course over time for estradiol plasters 6A to 6C. The measurement was made as described in Example 1 but using patches of size 5 $cm^2$ and a temperature of 34° C. The graph shows clearly the dependence of drug release on the type of water-swellable polymer used therein.

Comparison with Table 7 shows that drug release increases with increasing water absorption capacity of the used polymer material.

EXAMPLE 7

Propranolol patches with microcrystalline cellulose as water-swellable polymer product was manufactured as follows:

The propranolol containing adhesive material consists of

| propranolol micron. | 1.2 |
|---|---|
| microcrystalline cellulose (product AVICEL pH 105) | 1.2 g |
| three-block polystyrene/ poly/ethylene-butylene)/ | 3.71 g |

| polystyrene copolymer (product KRATON G 1657) | |
|---|---|
| solid aromatic hydrocarbon resin (product PICCOVAR L 60) | 5.0 g |
| liquid hydrocarbon mixture (product ONDINA OIL G 33) | 1.7 g |
| 1.2-propandiol | 0.34 g |
| special benzine 80–100 | 30 g |

The above adhesive material is coated onto a protective layer into consecutive partial steps onto a protective layer of which one side is vapour deposited with aluminum and both sides are abhesive in such a way that after evaporating of the solvent an adhesive film of about 13.1 mg/$cm^2$ is obtained. After applying an impermeable covering layer to cover the above-mentioned adhesive layer containing propanolol and swellable material, the patch film is divided into individual pieces suitable for therapeutic use.

DRUG RELEASE:

The determination is effected as described in Example 1 at 34° C. The cumulative drug release rates of the propanolol plasters according to the invention according to Example 7 have been determined as 5.64; 11.31; 20.0 and 26.79 mg/25 $cm^2$ after 2, 4, 8 and, respectively, 24 hours (mean values from two determinations).

EXAMPLE 8

A patch containing verapamil as active agent and galactomannane (product MEYPROGAT 90) as water-swellable polymer in a single layer matrix is produced as follows:

An adhesive material free of galactomannane consisted of 1.08 g of polyisobutylene (mean molecular weight of 900,000 to 1,400,000; trade product OPPANOL B 100)

1.35 g of solid aromatic hydrocarbon resin (trade product PICCOVAR L 60)

0.96 g of polyterpene resin (trade product DERCOLYT S 10)

0.24 g of polyethylene glycol (mean molecular weight of 300; trade product LUTROL 300)

0.30 g of 1:1-mixture of verapamil and siliciumdioxide (trade product AEROSIL 200)

10.0 g special benzine 80–110 as solvent.

The adhesive material is coated onto a protective layer of which one side is vapour deposited with aluminum and both sides are abhesive in such a way that after evaporating off the solvent and adhesive film of a weight per unit area of about 1.3 mg/$cm^2$ is obtained. Onto this so produced adhesive film the galactomannane containing matrix layer is coated with a weight per unit area of about 16.6 mg/$cm^2$. The production of this matrix layer is effected analogously from 10.8 g of polyisobutylene (mean molecular weight 900,000 to 1,400,000; trade product OPPANOL B 100)

13.5 g of solid aromatic hydrocarbon resin (trade product PICCOVAR L 60)

9.6 g of polyterpene resin (trade product DERCOLYTE S 10)

2.4 g of polyethylene glycol (mean molecular weight of 300; product LUTROL 300)

1.5 g of galactomannane (trade product MEYPROGAT 90)

12.0 g of 1:1-mixture of verapamil and siliciumdioxide (trade product AEROSIL 200)
100.0 g of special benzine 80–110.

The resulting film is covered with an impermeable cover layer and this final film is cut into pieces according to the therapeutical necessities.

EXAMPLE 9 (COMPARATIVE EXAMPLE)

The preparation is effected as described in Example 8, without however using galactomannane as water-swellable polymer.

DRUG RELEASE IN VIVO;

A patch of 5 cm$^2$ produced according to Examples 8 and 9 is fixed to the inner side of the forearm of the test person. 24 hours after application the patch was pulled off and the remaining amount of verapamil in the patch is determined chromatographically. The amounts of verapamil released were (a) for the patch according to Example 8 (containing galactomannane): 0.31 mg/cm$^2$
(b) for the patch according to Example 9 (free of galactomannane): 0.15 mg/cm$^2$.

These results show that the amount of in vivo drug release of verapamil is doubled by the use of the water swellable polymer galactomannane in patch formulations identical in other respects.

EXAMPLE 10

A patch containing bupranolol as active agent and microcrystalline cellulose (product AVICEL pH 105) as water-swellable polymer in an adhesive matrix layer is produced as follows:

A bupranolol containing rubber/adhesive resin material is produced consisting of

| | |
|---|---|
| bupranolol | 6.0 g |
| microcrystalline cellulose (product AVICEL pH 105) | 6.0 g |
| polyisobutylene product OPPANOL B 100) | 18.55 g |
| solid aromatic hydrocarbon resin (product PICCOVAR L 60) | 33.45 g |
| liquid hydrocarbon mixture (product ONDINA OIL G 33) | 11.1 g |
| 1.2-propandiol | 1.7 g |
| special benzine 80–110 | 191.15 g. |

The adhesive material containing bupranolol, comprising the constituents and solvent proportions given above, is coated onto a protective layer of which one side is vapour-deposited with aluminum and both sides are abhesive in such a way that after evaporating off the solvent an adhesive film of a weight per unit area of about 15.4 mg/cm$^2$ is obtained. After applying an impermeable covering layer to cover the above-mentioned adhesive layer containing bupranolol and microcrystalline cellulose as water-swellable material, the patch film is devided into individual pieces suitable for therapeutic use.

DRUG RELEASE IN VITRO;

The results are produced as described in Example 1 with a patch of 16 cm$^2$ in a phosphate buffer solution (pH=5.5) as drug release medium and at 34° C. The amounts of cumulative released active agent after 2, 4, 8 and 24 hours have been 3.12; 4.30; 5.89 and, respectively, 10.44 mg.

DRUG RELEASE IN VIVO;

At the lateral chest of 6 test persons each received a 25 cm$^2$ patch produced according to Example 10 each 24 hours over a total period of 3 days. Each 24 hours the patch was pulled off and the remaining content in bupranolol was determined chromatographically. The mean value of the individually released amount of active agent have been 13.49, 11.26; 13.70; 10.44; 14.76 and, respectively, 12.8 mg/25 cm$^2$/24 hours. Among these individual values the mean value has been 12.74±1.84 mg (n=3×6) bupranolol per patch.

This test shows a good reproducibility of the in vivo drug release and a comparatively good comparability of the corresponding in vitro values of 16.31 mg/25 cm$^2$/24 hours (=10.44 mg/25 cm$^2$/24 hours; see above).

BIOAVAILABILITY:

In the above described in vivo tests, blood samples have been collected 6, 12, 24, 36, 48, 60 and 72 hours after patch application and bupranolol plasma concentration has been determined radioimmunologically. The results are given in FIG. 3.

In accordance with this continues drug release a constant plasma level is produced during the application period of 3 days.

What we claim is:

1. In a transdermal drug patch for the controlled release of a drug to the human skin comprising:
   (a) an impermeable backing or covering layer,
   (b) a reservoir layer adjacent to, and in close contact with, said backing or covering layer, said reservoir layer comprising a polymer matrix composed of a rubber and an adhesive resin material in which a therapeutically active drug agent is present in wholly or partially soluble form and said material being permeable to said agent or agents,
   (c) an adhesive layer adjacent to, and in close contact with, said reservoir layer and permeable to said therapeutically active agent, and
   (d) a protective layer covering and adhearing to said adhesive layer and removable therefrom for the use of said transdermal drug patch, the improvement wherein said drug agent in the rubber and adhesive resin material of the reservoir layer is present together with a polymer capable of swelling in water and insoluble in the rubber and adhesive resin material of the reservoir layer, the quantity of said polymer being between 3 and 30 percent by weight of the rubber and adhesive resin mixture.

2. Transdermal drug patch according to claim 1 wherein the drug is a compound selected from the group consisting of the beta blockers, the steroid hormones, the calcium antagonists and the cardiac-acting drugs.

3. Transdermal drug patch according to claim 1 wherein the polymer capable of swelling in water and insoluble in the material of the reservoir layer and/or the adhesive layer is a polysaccharide or a mixture of polysaccharides.

4. Transdermal drug patch according to claim 2 wherein the polymer capable of swelling in water and insolule in the material of the reservoir layer and/or the adhesive layer is a polysaccharide or a mixture of polysaccharides.

5. Transdermal drug patch according to claim 2 wherein the polymer capable of swelling in water and insoluble in the material of the reservoir layer and/or the adhesive layer is a membrane selected from the group consisting of a galactomannane, microcrystalline cellulose and tragacanth.

6. Transdermal drug patch according to claim 3 wherein the polymer capable of swelling in water and insoluble in the material of the reservoir layer and/or the adhesive layer is a membrane selected from the group consisting of a galactomannane, microcrystalline cellulose and tragacanth.

7. Transdermal drug patch according to claim 4 wherein the polymer capable of swelling in water and insoluble in the material of the reservoir layer and/or the adhesive layer is a membrane selected from the group consisting of a galactomannane, microcrystalline cellulose and tragacanth.

8. Transdermal drug patch for estradiol according to claim 1 wherein the polymer capable of swelling in water and insoluble in the material of the reservoir layer and/or the adhesive layer is a galactomannane.

9. Transdermal drug patch for estadiol according to claim 2 wherein the polymer capable of swelling in water and insoluble in the material of the reservoir layer and/or the adhesive layer is a galactomannane.

10. Transdermal drug patch for estadiol according to claim 3 wherein the polymer capable of swelling in water and insoluble in the material of the reservoir layer and/or the adhesive layer is a galactomannane.

11. Transdermal drug patch for estadiol according to claim 4 wherein the polymer capable of swelling in water and insoluble in the material of the reservoir layer and/or the adhesive layer is a galactomannane.

12. Transdermal drug patch for estadiol according to claim 5 wherein the polymer capable of swelling in water and insoluble in the material of the reservoir layer and/or the adhesive layer is a galactomannane.

13. Transdermal drug patch for estadiol according to claim 6 wherein the polymer capable of swelling in water and insoluble in the material of the reservoir layer and/or the adhesive layer is a galactomannane.

14. Transdermal drug patch for estadiol according to claim 7 wherein the polymer capable of swelling in water and insoluble in the material of the reservoir layer and/or the adhesive layer is a galactomannane.

15. Transdermal drug patch for bupranolol according to claim 1 wherein the polymer capable of swelling in water and insoluble in the material of the adhesive film is microcrystalline cellulose.

16. Transdermal drug patch for bupranolol according to claim 2 wherein the polymer capable of swelling in water and insoluble in the material of the adhesive film is microcrystalline cellulose.

17. Transdermal drug patch for bupranolol according to claim 3 wherein the polymer capable of swelling in water and insoluble in the material of the adhesive film is microcrystalline cellulose.

18. Transdermal drug patch for bupranolol according to claim 4 wherein the polymer capable of swelling in water and insoluble in the material of the adhesive film is microcrystalline cellulose.

19. Transdermal drug patch for bupranolol according to claim 5 wherein the polymer capable of swelling in water and insoluble in the material of the adhesive film is microcrystalline cellulose.

20. Transdermal drug patch for bupranolol according to claim 6 wherein the polymer capable of swelling in water and insoluble in the material of the adhesive film is microcrystalline cellulose.

21. Transdermal drug patch for estadiol according to claim 7 wherein the polymer capable of swelling in water and insoluble in the material of the reservoir layer and/or the adhesive layer is a galactomannane.

22. Transdermal drug patch for nitroglycerin in accordance with claim 1 wherein the polymer capable of swelling in water and insoluble in the material of the matrix film and/or adhesive film is microcrystalline cellulose.

23. Transdermal drug patch for nitroglycerin in accordance with claim 2 wherein the polymer capable of swelling in water and insoluble in the material of the matrix film and/or adhesive film is microcrystalline cellulose.

24. Transdermal drug patch for nitroglycerin in accordance with claim 3 wherein the polymer capable of swelling in water and insoluble in the material of the matrix film and/or adhesive film is microcrystalline cellulose.

25. Transdermal drug patch for nitroglycerin in accordance with claim 4 wherein the polymer capable of swelling in water and insoluble in the material of the matrix film and/or adhesive film is microcrystalline cellulose.

26. Transdermal drug patch for nitroglycerin in accordance with claim 5 wherein the polymer capable of swelling in water and insoluble in the material of the matrix film and/or adhesive film is microcrystalline cellulose.

27. Transdermal drug patch for nitroglycerin in accordance with claim 6 wherein the polymer capable of swelling in water and insoluble in the material of the matrix film and/or adhesive film is microcrystalline cellulose.

28. Transdermal drug patch for nitroglycerin in accordance with claim 7 wherein the polymer capable of swelling in water and insoluble in the material of the matrix film and/or adhesive film is microcrystalline cellulose.

29. Transdermal drug patch for propranolol according to claim 1 wherein the polymer capable of swelling in water and insoluble in the material of the matrix film/adhesive film is microcrystalline cellulose.

30. Transdermal drug patch for propanolol according to claim 7 wherein the polymer capable of swelling in water and insoluble in the material of the matrix film/adhesive film is microcrystalline cellulose.

31. Transdermal drug patch for propanolol according to claim 3 wherein the polymer capable of swelling in water and insoluble in the material of the matrix film/adhesive film is microcrystalline cellulose.

32. Transdermal drug patch for propanolol according to claim 4 wherein the polymer capable of swelling in water and insoluble in the material of the matrix film/adhesive film is microcrystalline cellulose.

33. Transdermal drug patch for propanolol according to claim 5 wherein the polymer capable of swelling in water and insoluble in the material of the matrix film/adhesive film is microcrystalline cellulose.

34. Transdermal drug patch for propanolol according to claim 6 wherein the polymer capable of swelling in water and insoluble in the material of the matrix film/adhesive film is microcrystalline cellulose.

35. Transdermal drug patch for propranolol according to claim 7 wherein the polymer capable of swelling in water and insoluble in the material of the matrix film/adhesive film is microsrystalline cellulose.

* * * * *

UNITED STATES PATENT AND TRADEMARK OFFICE
CERTIFICATE OF CORRECTION

PATENT NO. : 4,668,232

DATED : May 26, 1987

INVENTOR(S) : Cordes et al

It is certified that error appears in the above-identified patent and that said Letters Patent is hereby corrected as shown below:

Column 12, Claim 1, line 42, "adhearing" should be --adhering--.

Column 12, Claim 4, line 63, "insolule" should be --insoluble--.

Column 14, Claim 35, line 67, "microsrytalline" should be --microcrystalline--.

Signed and Sealed this

Twenty-ninth Day of September, 1987

Attest:

DONALD J. QUIGG

Attesting Officer     Commissioner of Patents and Trademarks